United States Patent [19]
Laderoute

[11] Patent Number: 5,230,707
[45] Date of Patent: Jul. 27, 1993

[54] LIMITED USE HYPODERMIC SYRINGE

[76] Inventor: Maurice Laderoute, 118 Samosette Ave., Hull, Mass. 02045

[21] Appl. No.: 587,181

[22] Filed: Apr. 30, 1990

Related U.S. Application Data

[62] Division of Ser. No. 222,553, Jul. 21, 1988, Pat. No. 4,946,441.

[51] Int. Cl.$^5$ ............................................. A61M 37/00
[52] U.S. Cl. ........................................ 604/86; 604/415
[58] Field of Search ................. 604/86, 165, 167, 403, 604/411, 187, 415

[56] References Cited

U.S. PATENT DOCUMENTS

| 4,121,585 | 10/1978 | Becker, Jr. | 604/86 |
| 4,219,912 | 9/1980 | Adams | 604/86 |
| 4,289,129 | 9/1981 | Turner | 604/86 |
| 4,619,651 | 10/1986 | Kopfer et al. | 604/415 |
| 4,966,588 | 10/1990 | Rayman et al. | 604/167 X |

FOREIGN PATENT DOCUMENTS

| 1054174 | 2/1954 | Fed. Rep. of Germany | 604/86 |
| 2805354 | 9/1978 | France | 604/86 |

Primary Examiner—John D. Yasko
Attorney, Agent, or Firm—Ellen C. Childress

[57] ABSTRACT

A hypodermic syringe which can be filled with liquid medication for injection into a subject only from a container of the liquid under pressure greater than the ambient pressure around the syringe includes a moveable piston in a cylinder and an injection needle extending from one end of the cylinder defining a liquid dosage space between the piston and the needle and on the other side of the piston in the cylinder is a piston stem that extends from the other end of the cylinder and is manipulated by the user to inject a liquid from the dosage space under the force of the piston out of the needle, the piston and the piston stem being adapted so that the stem can be manipulated to push the piston toward the needle, but the stem cannot be manipulated to pull the piston away from the needle, and the position of the stem in the cylinder can be adjusted at any of a plurality of positions that limit the travel of the piston away from the needle and so limit the volume of the liquid dosage space defined between the piston and the needle. In preferred embodiments, the limitation adjustment is continuously variable at all values of dosage space volume from substantially zero to a predetermined maximum volume.

11 Claims, 3 Drawing Sheets

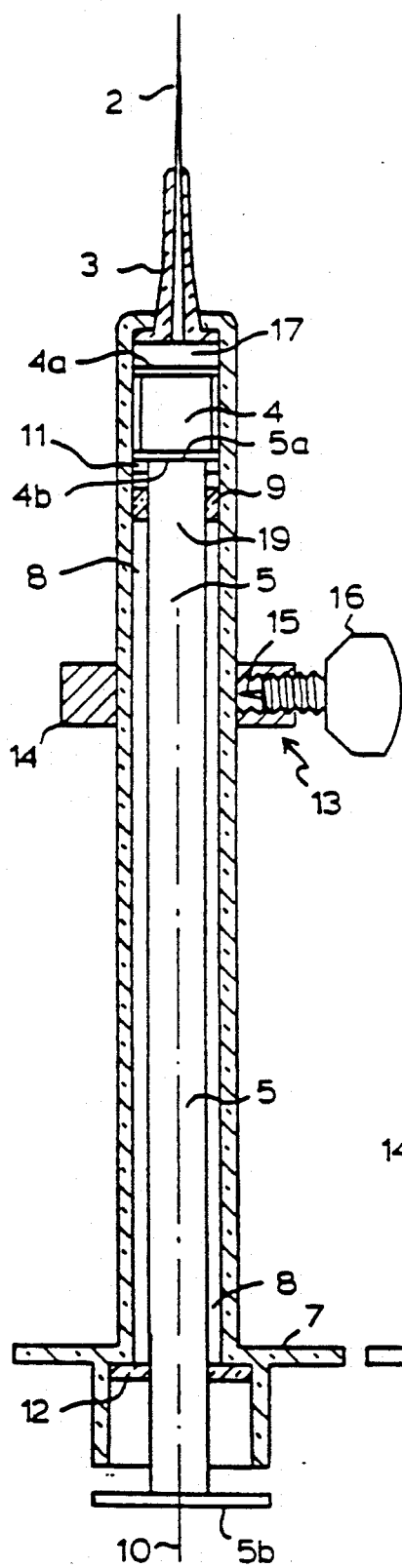
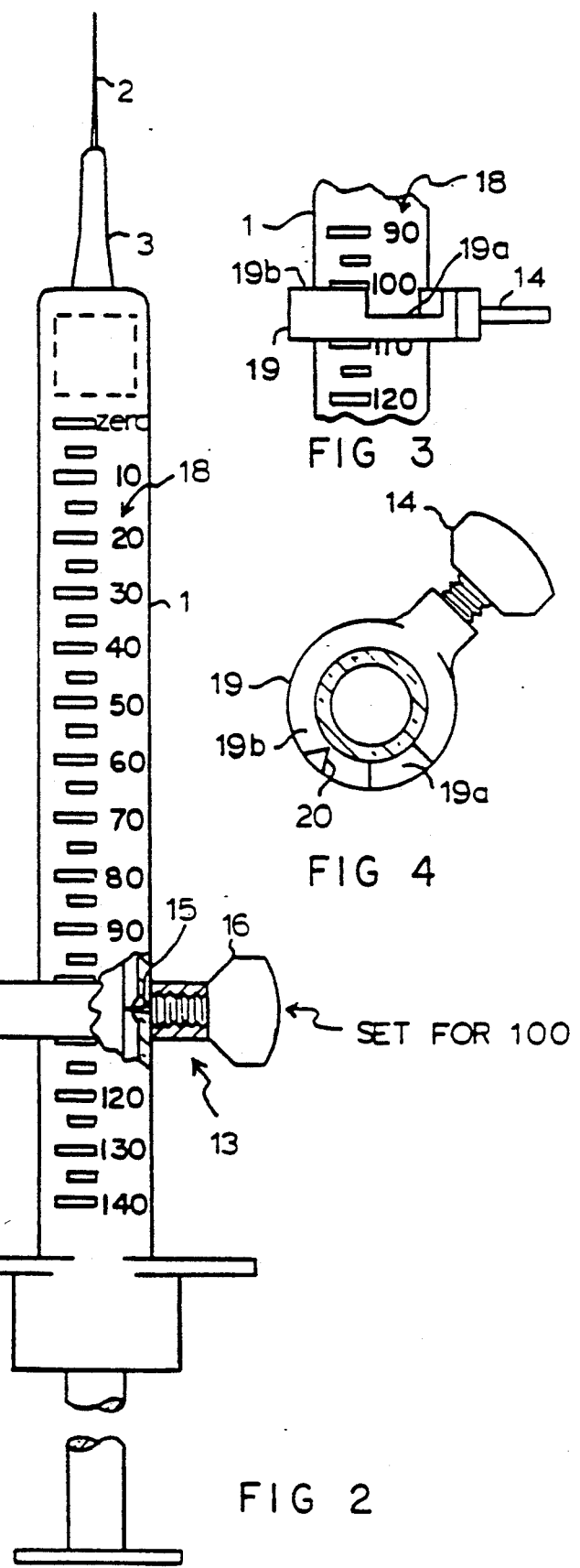

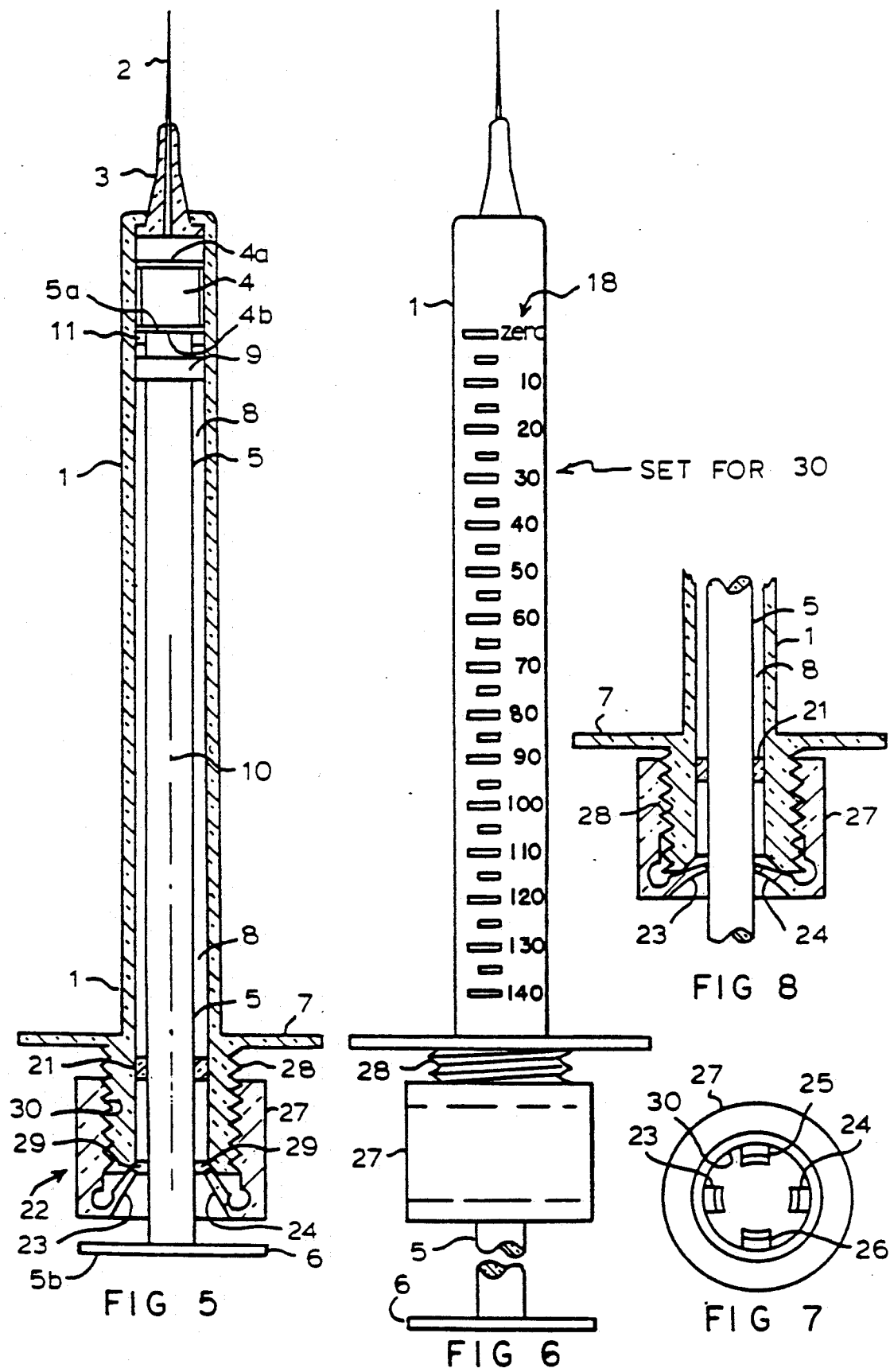

LIMITED USE HYPODERMIC SYRINGE

This is a division of application Ser. No. 222,553, filed Jul. 21, 1988 now U.S. Pat. No. 4,946,441.

FIELD OF THE INVENTION

The present invention relates to hypodermic syringes of the type that are filled with liquid medication from a vial of the liquid that is pressurized to a pressure greater than the pressure within the syringe.

BACKGROUND OF THE INVENTION

Most syringes for hypodermic injection of a liquid into a subject are capable of repeated use if a user so desires, or the syringe can be destroyed by the user so that it cannot be used again.

The need for a hypodermic syringe that cannot be reused has become particularly important in view of the repeated reuse of discarded hypodermic syringes by drug addicts without proper sterilization between each use. Blood born infectious diseases are spread between drug addicts that share a syringe. This has been identified as a major cause of the spread of hepatitis, venereal disease, and AIDS among drug addicts. Drug addicts are known to rummage through the trash of a hospital in an effort to find discarded syringes. Clearly, that source of syringes for illicit use by drug addicts would be stopped if all syringes were destroyed after use and before being discarded.

Heretofore this problem has been addressed time and again in efforts to provide a non-reusable syringe and in all of those efforts attention is paid to the way the drug addict uses the discarded syringe and the effort is made to redesign the syringe so that it cannot be used in that way. The usual illicit use of a hypodermic syringe involves filling the syringe with liquid for injection from an open vessel, which is done by inserting the syringe needle into the liquid and drawing back the syringe piston creating a slight vacuum in the syringe so that liquid from the vessel flows under atmospheric pressure through the needle into the syringe.

A very simple way to frustrate this illicit use it to break of destroy the needle of the syringe or destroy the piston or destroy the cylinder. These "destroy" techniques are not automatic and so the destruction is discretionary with the user. A more subtle technique provides a plunger that can be retracted only once. More particularly, after a first retraction and injection by a legitimate user, the piston cannot be withdrawn again to draw in another charge of liquid for injection, because the stem attached to the piston hits against a stop. Unfortunately, the stop can be tampered with and made ineffective and so the syringe can be used again when that is done.

Thus, while some of the techniques used in the past to provide a non-reusable syringe are automatic and are not discretionary with the first user, they can be tampered with by a drug addict and the syringe used again. The other techniques that destroy useful parts of the syringe are quite effective provided they are carried out and since all are discretionary with the first user, such syringes that come initially into the hands of a drug addict never get destroyed and are passed around and give rise to the problem.

It is an object of the present invention to provide a hypodermic syringe that cannot be used in the conventional way that hypodermic syringes are used by drug addicts, and, in particular, cannot be filled with liquid for an injection from an open vessel.

It is an object of the present invention to provide a hypodermic syringe that does not depend upon a discretionary act of the first user to limit the usefulness of the syringe for illicit use by a drug addict.

It is another object of the present invention to provide a hypodermic syringe that is not reusable by any conventional way that drug addicts use a syringe and where that condition does not depend upon a discretionary action by a first user, and so some of the limitations mentioned above of prior non-reusable syringes are avoided.

It is another object to provide a hypodermic syringe that is intrinsically less useful for illicit uses, because the syringe piston cannot be withdrawn to draw by vacuum a liquid into the syringe, while the syringe can be used repeatedly by those having facilities for loading the syringe with liquid from a pressurized rubber diaphragm vial of the liquid.

SUMMARY OF THE INVENTION

All embodiments of the present invention provide a hypodermic syringe which can only be filled with liquid medication for injection into a subject from a rubber syringe pushing the piston away from the needle until it abuts the stem; insert the needle into the subject; and manually drive the stem relative to the cylinder against the piston forcing the dosage liquid through the needle into the subject.

Also, in preferred embodiments, a scale is provided along the cylinder with marks indicating the liquid dosage volume and means are provided for stopping the longitudinal position of the stem in the cylinder so that the liquid dosage space volume defined when the piston abuts the stem is at a particular selected value shown on the scale. In one embodiment, that means for stopping includes a stop ring attached to the stem at the end of the stem that abuts the piston and fits in the annular space between the stem and the inside of the cylinder, in combination with means carried on the outside of the cylinder that is positionable at any point along the cylinder and carries a probe that can be manipulated to penetrate through the cylinder wall into the annular space and so limit the maximum withdrawal position of the stem from the cylinder and so set the maximum dosage space volume.

According to another embodiment, means are provided at the open end of the cylinder for positioning a continuous ratchet type device against the stem where the stem emerges from the open end of the cylinder so that the continuous ratchet type device prevents the further withdrawal of the stem from the cylinder and yet does not inhibit inserting the stem further into the cylinder and driving the piston toward the needle.

All embodiments of the present invention require a pressurized rubber diaphragm vial of the liquid medication to fill the syringe with the desired dosage volume and the vial must be pressurized to a pressure greater than the pressure in and around the syringe (usually ambient pressure). Such containers are in ready supply for legitimate use in the form of glass bottles with a single neck and opening in which a rubber diaphragm stopper is inserted and held in place by a metal (aluminum) cap that is press fit onto the stopper and around the neck of the bottle. These are called rubber diaphragm medication vials. An opening at the center of the metal cap provides access to the center part (target area) of the rubber diaphragm. Access to the interior of the vial is achieved by inserting a hollow needle through the rubber diaphragm into the bottle and the rubber seals around the needle so that air borne contamination cannot enter the vial.

The advantage of this type vial of encapsulated liquid medication is that the vial remains sealed at all times against ambient air and the seal is not broken when the inside of the bottle is accessed with a syringe needle, because the needle penetrating the stopper is sealed against by the stopper as the needle penetrates the stopper and since the pressure in the vial is greater than the pressure inside the syringe, there is no flow of gas or liquid into the vial through the needle.

Such rubber diaphragm vials are used quite widely for the legitimate administering of drugs and medication by a hypodermic syringe. The vial require periodic renewing of the gas pressure inside as the contents of the vial are withdrawn by hypodermic syringe for use. The pressure is replenished using a special hand pump with a needle output and is valved so that it can be stroked several times to increase the pressure inside the vial. The pump is preferably filled with sanitized air or contains means to sanitize the air it is filled with.

Following that the hypodermic syringe is inserted through the same stopper and since the pressure inside the bottle is now greater than ambient the liquid flows from the bottle into the syringe through the syringe needle. In this way the medication is maintained in an air tight seal under pressure and ready for use.

Some of the limitations and inconveniences of the available rubber diaphragm vials are: the pump needle and the hypodermic syringe needle to be filled with the liquid medication are inserted through the same rubber diaphragm stopper and so care must be taken that the pump needle emerges in the vial air pocket and that the syringe needle emerges in the vial liquid and this may require turning the vial and carefull scrutiny by the user; and the rubber diaphragm that may be ideal for the very small hypodermic needle is not ideal for the much larger pump needle and vice versa. Another problem that arises particularly for infirm people who administer medication to themselves by hypodermic syringe is that the diaphragm target that the syringe needle is inserted through is small and sometimes difficult to hit by a person with poor eyesight or a trembling hand.

It is another object of the present invention to provide a rubber diaphragm vial type of liquid medication bottle wherewith some of the above mentioned difficulties and limitations of such vials and the usage of the same are avoided.

It is another object to provide a rubber diaphragm vial type of medication bottle having separate needle penetratable stoppers for a pump needle and for a hypodermic syringe needle located with respect to each other where they are most conveniently used to increase gas pressure inside the bottle by inserting the pump needle or to extract a dosage of the medication from the bottle with a hypodermic syringe.

These and other objects and advantages of the present invention will become apparent from the following specific description of embodiments of the invention and the appended claims.

DESCRIPTIONS OF THE DRAWINGS

FIGS. 1 and 2 are plan cross-section and plan partially cross-section views, respectively, of a hypodermic syringe incorporating features of the present invention and shown longitudinally upright with the needle thereof pointing upward and including structure for limiting the input dosage volume in the syringe moveably located along the syringe cylinder on a volume scale marked therealong;

FIGS. 3 and 4 are plan and top views, respectively, of another form of the structure shown in FIGS. 1 and 2 for varying the maximim intake volume of the syringe;

Figure 9:
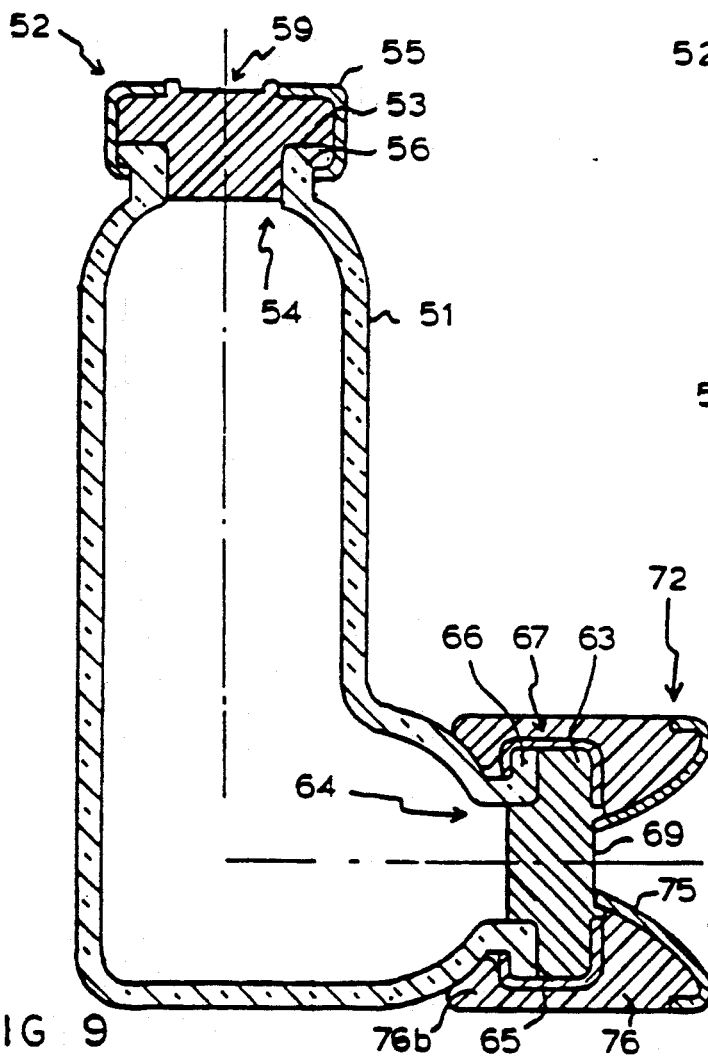
Figure 10:
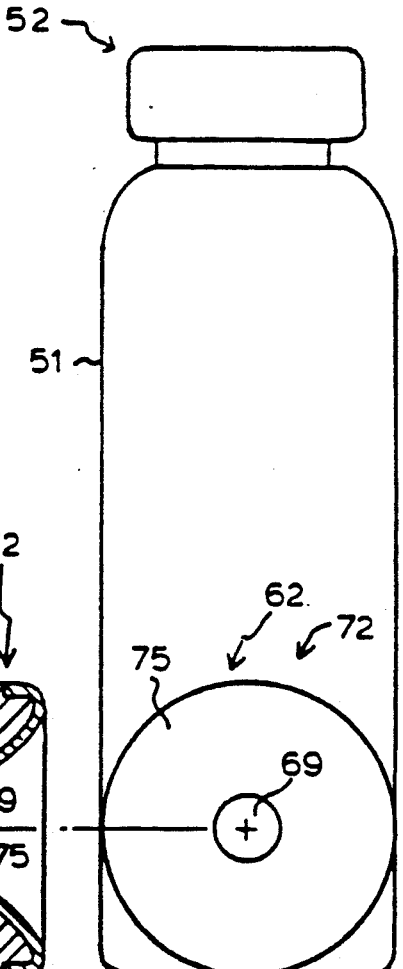
Figure 11:
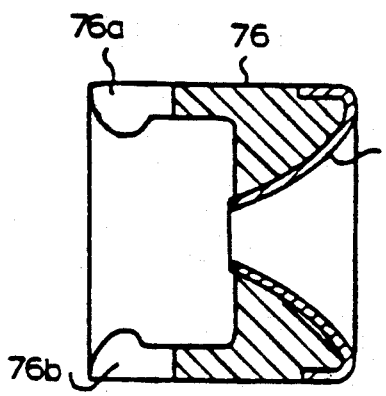
Figure 12:
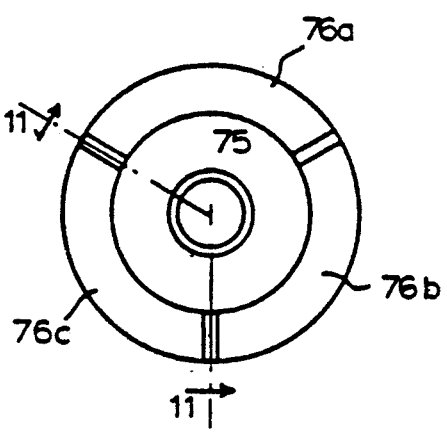

FIGS. 5 and 6 are fully cross-section and non-cross-section, respectively, plan views of another embodiment of hypodermic syringe oriented longitudinally upright with the needle thereof pointing upward wherein the means for setting maximum intake dosage volume includes a continuous ratchet type stem stop mechanism at the output end of the cylinder that is manipulated by turning to inhibit further withdrawal of the stem from any desired longitudinal position within the syringe cylinder;

FIG. 7 is a bottom end view of the continuous ratchet type stem stop mechanism;

FIG. 8 is a plan cross-section view showing the continuous ratchet type stem stop mechanism manipulated to a position where the stem is stopped and cannot be further withdrawn from the cylinder, but is readily moveable into the cylinder;

FIG. 9 is a plan cross-section view of a rubber diaphragm vial type of liquid medication bottle oriented upright with a diaphragm for access by a pump needle at the top, a diaphragm for access by a hypodermic syringe at the bottom and a special guide attachment enabling easy access to the target area of the hypodermic syringe diaphragm;

FIG. 10 is a side view of the rubber diaphragm vial type liquid medication bottle of FIG. 9; and FIGS. 11 and 12 are plan cross-section and end views, respectively, of the special guide attachment to the syringe access stopper.

DESCRIPTION OF EMBODIMENTS OF THE INVENTION

The various embodiments of the present invention described herein and shown in the several figures include a number of assemblies, parts and members which are essentially the same in each embodiment. Therefore, those that are the same will bear the same general reference number and where a given part thereof varies from one embodiment to another only the given part that is different will bear a different reference number.

All of the embodiments that describe a hypodermic syringe are referred to herein as a hypodermic syringe having limited use. By limited use, it is meant that the syringe can only be filled with a liquid to be administered from a pressurized vial of the liquid that can be accessed by inserting the syringe needle through a rubber diaphragm of the pressurized vial. Inasmuch as such a vial for liquid medication is usually not part of a drug addicts' paraphernalia for illegal use of drugs, these embodiments of the present invention are also referred to as being non-reusable for illicit injecting of drugs.

Hypodermic Syringe - First Embodiment

Turning first to FIGS. 1 and 2 there are shown two views of a hypodermic syringe including a cylinder or barrel 1 open at one end (the bottom end) and restricted at the other end (the top end) by the needle assembly 2. At the restricted end, the needle is embedded in the needle base 3 which is sealed to the top end of the cylinder. The inside of the cylinder is of uniform cross-section from the restricted end to the open end so that the piston 4 is moveable therethrough under force supplied to the piston via the piston stem 5 against the backface 4b of the piston or by a fluid force against the front face 4a of the piston.

Piston 4 fits snugly around the perimeter of both the front face 4a and the back face 4b against the inside wall 1a of the syringe cylinder forming at least a liquid tight seal therewith and preferably forming a gas tight seal therewith. To ensure such a seal the piston may be made of resilient rubber and the syringe cylinder may be made of relatively rigid plastic or it may be made of glass.

The front face 5a of piston stem 5 abuts the back face 4b of the piston and the back face 5b of the stem emerges from the open end of the cylinder and may include a flange 6 to facilitate manual manipulation of the stem. Also, a flange 7 may be provided at the open end of the cylinder to further enable manual manipulation of the stem relative to the cylinder.

Piston stem 5 fits easily longitudinally within cylinder 1 and defines an annular space 8 between the stem and the inside walls 1a of the cylinder and annular space 8 is uniform throughout the length of the cylinder. At the front end of stem 5, attached to the stem is the stem stop ring 9 that moves through the annular space 8 freely as the stem is inserted or withdrawn from the cylinder. At the front face 5a of the stem that abuts the back face 4b of piston 4 there may be provided lateral protuberances such as 11 on the stem that increase the stem contact area with the back face 4b of piston 4. At the open end of cylinder 1 projecting into annular space 8 and attached to the cylinder is another stop 12 for the stem that limits withdrawal of the stem from the cylinder when stop 9 abuts stop 12.

The arrangement of all parts mentioned above and shown in FIG. 1 is such that stem 5 can be freely moved longitudinally within cylinder 1 toward or away from piston 4. It can be freely moved toward the piston until contacting the back face 4b of the piston and then continued in that direction until the front face 4a of the piston meets needle base 3. Also, stem 5 can be withdrawn from the cylinder and moved away from the piston until stop 9 attached to the stem meets stop 12 attached to the cylinder. To facilitate this movement of the stem within the cylinder, the user may use flanges 6 and 7 with the middle and fourth finger on flange 7 and thumb on flange 6 to push the stem toward the piston and the user may use both hands to withdraw the stem from the cylinder away from the piston.

A variable stop is also provided for stem stop ring 9 in the annular space 8. The variable stop assembly 13 includes a ring 14 that slides along the outside of cylinder 1 and carries a probe 15 at the end of thumb screw 16. Ring 14 is positioned along cylinder 1 where the stop is desired and thumb screw 16 is screwed into the ring so that probe 15 penetrates the wall of cylinder 1 and projects into annular space 8. The penetrating probe 15 acts as a stop for stem stop ring 9 and so fixes the maximum withdrawal position of the stem in the cylinder when the syringe needle is inserted into a rubber diaphragm vial to fill the syringe More particularly, liquid from the vial flows through needle 2 into the dosage space 17 defined by piston front face 4a and needle base 3. The liquid under pressure from the vial flows into space 17 forcing the piston against the stem and moving both together toward the other end of the cylinder until stem stop 9 meets penetrating probe 15. The syringe is then filled with the desired dose.

FIG. 2 shows the same hypodermic syringe with a dosage volume scale 18 on the outside of the cylinder. In this figure the variable stop assembly 13 is set at a reading of 100 and the penetrating probe 15 penetrates the cylinder wall at the mark 100 and so sets the stop at 100. The scale 18 is so arranged that the volume of fluid between piston face 4a and needle base 3 is 100 units of volume. The user can then administer the injection and inject all or any part of the 100 units. If part of the 100 units are injected, the user can determine how many units are injected by noting the position of dark line 19 along scale 18. For that purpose, cylinder 1 must be transparent.

If the user injects some of the 100 units and then desires to refill the syringe to the 100 units, the user need only reinsert the syringe into the rubber diaphragm vial containing the medication and the syringe will fill up again to the 100 mark. The user can also reset variable stop 13 to a volume dosage that is lower than the one initially set (100 in this example); however, since stop 13 punctures the cylinder wall each time it is set, it cannot be reset at a greater volume dosage than the initial set.

Clearly, the syringe cannot be filled at any time by drawing liquid in through the needle into a relative vacuum created in space 17, because the piston cannot be pulled by the stem, it can only be pushed by the stem.

An alternate variable stop assembly 13 of this embodiment is shown in FIGS. 3 and 4. Here the ring 19 has a notch or cut out 19a in the top surface 19b allowing a clear view of the dosage volume scale number on the outside of the cylinder. As shown in FIG. 3, the scale number is 100 units and the stop is aligned with 100 when the top surface 19a of the ring is even with the mark alongside the number. An arrow 20 may be provided on the top surface of ring 19 aligned with the volume number mark.

To ensure that air is not trapped in annular space 8 that might impede movement of the stem in and out of the cylinder, the stem stop 9 and cylinder stop 12 may both be perforated longitudinally so that they act only as mechanical stops and do not impede the flow of air displaced in the annular space when the syringe is used.

Limited Use Hypodermic Syringe - Second Embodiment

Turning next to FIGS. 5 to 8 there is shown another embodiment of a hypodermic syringe incorporating features of the invention. Here, the structure is the same as in the embodiment shown in FIGS. 1 and 2 except at the open end of cylinder 1, below flange 7, another mechanism is provided for stopping the stem and serves essentially the same function as variable stop assembly 13. Here, stop 9 at the upper end of stem 5 serves only to abut cylinder stop 21 at the open end of the cylinder and so prevent the stem from being fully withdrawn from the cylinder. At all other positions between full insertion of the stem up the cylinder, to withdrawal of the stem to stop 21, the stem is stopped to prevent further withdrawal of the stem by the continuous ratchet operation of the variable stop assembly 22 at the open end of the cylinder. The continuous ratchet operation is accomplished by fingers 23 to 26 that extend radially inwardly on the inside of nut 27 that screws onto threaded coaxial boss 28 that extends downward from flange 7 and is a continuation of cylinder 1. When nut 27 is screwed onto threaded boss 28 as shown in FIG. 5 so that the fingers 23 to 26 do not touch the beveled inside face 29 at the end of threaded boss 28, the fingers are tilted more upward and do not touch piston stem 5. However, when nut 27 is screwed onto boss 28 further as shown in FIG. 8, the fingers encounter bevel face 29 and are bent downward and inward so that they project against the stem as shown in FIG. 8. In this position, the fingers act like engaging palls of a continuous ratchet and prevent withdrawal of the stem from the cylinder; however, they do not prevent inserting the stem further into the cylinder. This pall action can be released by simply screwing nut 27 off of boss 28 so that the fingers return to the position shown in FIG. 5 where they do not contact the bevelled edge 29 sufficiently to be bent against the stem. A top view of nut 27 removed from boss 28 illustrared in FIG. 7 shows the four pawl-like fingers 23 to 26.

The hypodermic syringe shown in FIGS. 5 to 8 is used in much the same way as the syringe shown in FIGS. 1 and 2. To fill the syringe from a rubber diaphragm vial that has been pressurized, first the stem is positioned in the cylinder by inserting it or withdrawing it and noting the position of the stem stop ring 9 along scale 18 on the outside of cylinder 1. For this purpose the cylinder may be transparent and stop ring 9 may be colored dark so that it can be seen through the cylinder and, in fact, the entire stem may be a dark color so that from the outside the scale appears dark up to the top of ring 9. As shown in FIG. 6 the stem is set so that the top of ring 9 aligns with the mark alongside, for example, dosage volume of 30 units. At that desired setting of the stem, nut 27 is screwed onto boss 28 bending fingers 23 to 26 against the stem and locking the stem in that position so that it cannot be further withdrawn from the cylinder, even while not inhibiting the stem from being inserted further into the cylinder. Then, the syringe needle is inserted into the rubber diaphragm vial containing liquid at pressure and immediately the liquid flows into space 17 of the syringe filling that space and forcing the piston against the front face 5a of the stem. When the piston reaches the stem set at the scale number 30, the volume of space 17 is 30 units and so it holds 30 volume units of the liquid medication. Meanwhile the palls 23 to 26 against the stem prevent the piston from pushing the stem further out of the cylinder. In this way the syringe is filled to a preset volume of medication liquid and will not fill beyond that volume.

Thereafter, without releasing nut 27, the syringe can be used to inject all or part of the liquid in one or more sequential steps. However, during that process the syringe cannot be refilled back to the level of 30 units of volume, because the pawls 23 to 26 still prevent the stem from being withdrawn from the cylinder. In this embodiment, in order to refill the syringe, the pawls must be released by unscrewing nut 27 and then reposition the stem and again tighten nut 27 to reset the pawls against the stem. Clearly, the stem can be reset at any scale value, even one greater than the initial set, as there is no perferation of the cylinder.

Comparison of Operations of First and Second Embodiments

Uses of the first and second embodiments of hypodermic syringe according to the present invention can be compared as follows:

| First Embodiment | Second Embodiment |
| --- | --- |
| (a) after first set of stop 13, | (a) after first set of stop 22 |
| syringe can be unloaded and reloaded as many times as desired without resetting 13; | syringe can be unloaded, but cannot be reloaded without releasing 22; |
| (b) after first set of stop 13 stop 13 can be released, but cannot be reset at a greater value than the first set; and | (b) after first set of stop 22 stop 22 can be released and reset at a greater value than first set; and |
| (c) setting stop 13 partially destroys the syringe. | (c) setting, releasing and resetting stop 22 in no way destroys the syringe. |

Dual Rubber Diaphragm Vial

Turning next to FIGS. 9 through 12 there is shown a specially adapted rubber diaphragm vial containing liquid medication that is administered using a hypodermic syringe such as those described herein. The body 51 of the vial is preferably made of glass and has two openings, a pump needle access opening 54 at the top and a hypodermic syringe needle access opening 64 at the bottom, both stoppered with a rubber diaphragm stopper designed for penetration with a needle. At the top opening, the pump needle access rubber diaphragm stopper assembly 52 includes a pump needle rubber diaphragm stopper 53 that plugs the opening neck at the top is secured in place by a metal cap 57, preferably made of aluminum, that folds around the vial lip 56 and around the top of diaphragm 53 leaving a target area 59 of the diaphragm for access to the inside of the vial by a pump needle that is thrust through the diaphragm at the target area.

At the bottom of the vial, the hypodermic syringe needle access opening 64 is preferably oriented perpendicular to the top pump needle access opening 54. Opening 64 is capped by a hypodermic syringe needle access rubber diaphragm stopper assembly 62. At the bottom opening, the assembly 62 includes a hypodermic syringe needle access rubber diaphragm stopper 63 that plugs the opening neck and is secured in place by a metal cap 67, preferably made of aluminum, that folds around the vial lip 66 and around the top of diaphragm stopper 63 leaving a target area 69 of the diaphragm for access to the inside of the vial by a hypodermic syringe needle that is thrust through the diaphragm at the target area.

Clearly, rubber diaphragm stopper 53 is penetrated with a pump needle to pump gas into the vial to increase the vial pressure and rubber diaphragm 63 is used to withdraw liquid from the vial by a hypodermic syringe. As described hereinabove with reference prior devices, rubber diaphragm vials are pressurized using a special pump that has a needle for penetrating the rubber diaphragm. According to the present invention, the pump needle be inserted through a different rubber diaphragm to pump gas into the vial than the diaphragm through which the hypodermic syringe is inserted to withdraw liquid from the vial and there are several reasons why this arrangement is preferred.

The rubber diaphragm vial shown in FIGS. 9 and 10 is used most advantageously by inserting the pump needle through pump needle access stopper 54 into the gas space in the vial to pump up the pressure therein and then inserting the hypodermic syringe needle to be filled with the liquid medication through syringe needle access stopper 64 into the liquid space in the vial to fill the syringe. This can be simultaneously, whereby the pump needle is withdrawn before the syringe needle is inserted, or it can be done simultaneously, whereby the syringe needle is inserted while the pump needle is still inserted and pumping can be done before and after the syringe needle is filled.

Regardless of the sequence for pumping and filling the syringe, the rubber diaphragm vial shown in FIGS. 9 and 10 avoids the necessity of turning the vial and carefull scrutiny by the user to insure that the pump needle is inserted only into the air space in the vial and the syringe needle is inserted only into the liquid in the vial. Furthermore, a rubber diaphragm that may be ideal for the very small hypodermic syringe needle, is not ideal for the much larger pump needle and vice versa. These problems arise with the conventional rubber diaphragm stopper vial, particularly for infirm people who administer medication to themselves by hypodermic syringe and are avoided with the vial shown in FIGS. 9 and 10.

Funnel Device To Aid Needle Insertion Into Vial

Another problem that arises, particularly for infirm people who administer medication to themselves by hypodermic syringe is that the diaphragm target that the syringe needle is inserted through is small and sometimes difficult to hit by a person with poor eyesight or a trembling hand. Hypodermic syringes are frequently quite small, particularly the disposable syringes. For example, the needle may be only a half inch long and the cylinder less than a quarter inch in diameter and no more than three inches long. People who use such hypodermic syringes often administer injections to themselves and so they suffer some disabilities that require the injections as a treatment. For example, diabetics who often suffer poor eyesight inject themselves daily with human insulin provided in small rubber diaphragm vials containing 10 to 20 ml. On such vials the target area 69 of the rubber diaphragm is quite small, often no more than an eighth inch in diameter and the user may find it difficult to align the syringe needle with the target and insert it through to withdraw liquid insulin from the vial.

To aid in that effort a special funnel assembly 72 is provided that fits over the hypodermic syringe rubber diaphragm assemble 62 used to fill a syringe with liquid insulin from the vial. The funnel assembly includes a flexible plastic funnel holder 76 with flexible fingers 76a, 76b and 76c that spread to fit around the diaphragm assembly and then close around the outside of neck 64 to fit the funnel assembly securely to the neck of the vial. On the opposite side of the funnel assembly the holder is shaped in the form of a funnel that leads from a large target area to the small target area 69 of the diaphragm. A stainless steel funnel piece 75 fits the funnel contour and tends to guide the syringe needle to the target area 69 when inserted toward that area by the user.

Clearly, a funnel assembly like 72 can also be attached to the rubber diaphragm assembly 52 at the top of the vial to aid inserting the pump needle into the vial.

The several embodiments of a hypodermic syringe described herein have in common a syringe cylinder, needle, piston and piston stem that extends from the open end of the cylinder, the piston stem and piston being so adapted that movement of the stem toward the needle can move the piston toward the needle, but movement of the stem away from the needle cannot move the piston away from the needle, and the piston can be moved away from the needle to increase the volume of the dose liquid in the syringe only by inserting the needle into a liquid at a greater pressure than the ambient pressure around the syringe. These embodiments describe several structures for setting the dosage volume of the syringe to fill the syringe with that volume of liquid and each has certain advantages with respect to the other and both have advantages over the prior art. Another invention disclosed herein is a novel rubber diaphragm stopper vial including separate diaphragms for pumping pressure and for withdrawing liquid from the vial and a separable funnel assembly to aid those of limited ability to readily use the vial with competence and efficiency. It is to be understood that additional embodiments and variations of these inventions will be obvious to those skilled in the art and the embodiments described herein together with those additional variations are considered to be within the scope of the inventions.

What is claimed is:

1. In combination with a hypodermic syringe for injection of a liquid dosage into a predetermined relatively small area of an object the hypodermic syringe including a cylinder having an open end and an restricted end, a hollow needle at said cylinder restricted end for discharging liquid from said syringe, a piston having a front end and a back end said piston being slidably positioned within said cylinder forming a liquid tight seal with the interior of said cylinder and defining a liquid dosage space between said piston front end and said needle, a piston stem slidable within said cylinder on the back end side of said piston said piston stem back end extending beyond said cylinder open end, said stem being movable towards said open end of said cylinder and said stem being movable toward said piston back end moving said piston towards said needle forcing dosage liquid from said dosage liquid space through said hollow needle a guide for aiding the manual insertion of said syringe needle into said relatively small target area of said object, comprising, (a) a tapered tubular guide body having an open guide end and a target end, said target end being aligned with and in registration with said relatively small target area, (b) the area of said open guide end being many times greater than the area of said target end, and (c) the inside surface of said tapered tubular guide body being sufficiently smooth and hard that the point of said needle readily slides along said surface from said guide end to said target end when the syringe is thrust into said guide (d) whereby said point of said syringe needle thrust into said guide is compelled to penetrate said body at said target area thereof.

2. The combination in claim 1 wherein,
(a) said vial body is adapten to stand with said top part above said bottom part.

3. The combination in claim 1 wherein,
(a) said first hypodermic syringe needle access opening is oriented perpendicular to said second pump needle access opening.

4. The combination in claim 1 wherein,
(a) said first hypodermic syringe needle access opening is oriented vertical and said second pump needle access opening is oriented horizontal.

5. The combination in claim 2 wherein,
(a) said first hypodermic syringe needle access opening is below said second pump needle access opening when said vial stands as it is adapted on a level surface.

6. The combination in claim 1 wherein,
(a) said vial body is adapten to stand with said top part above said bottom part,
(b) said first hypodermic syringe needle access opening being oriented perpendicular to said second pump needle access opening and
(c) said first hypodermic syringe needle access opening is oriented vertical and said second pump needle access opening is oriented horizontal.

7. The combination in claim 1 wherein,
(a) said first hypodermic syringe needle access opening is oriented perpendicular to said second pump needle access opening,
(b) said first hypodermic syringe needle access opening is oriented vertical and said second pump needle access opening is oriented horizontal and
(c) said first hypodermic syringe needle access opening is below said second pump needle access opening when said vial stands as it is adapted on a level surface.

8. In combination with a hypodermic syringe for injection of a liquid dosage into a predetermined relatively small target area of an object, a guide consisting essentially of:
(a) a tapered tubular guide body having an open guide end and a target end, said target end being aligned with and in registration with said relatively small target end,
(b) the area of said open guide end being many times greater than the area of said target end, and
(c) the inside surface of said tapered tubular guide body being sufficiently smooth and hard that the point of said needle readily sides along said surface from said guide end to said target end when the syringe is thrust into said guide,
(d) whereby said point of said syringe needle thrust into said guide is compelled to penetrate said body at said target area thereof,
(e) wherein said tapered tubular guide is adapted for attachment to said object so as to place said target end thereof aligned with and in registration with said relatively small target area of said object, wherein said tapered tubular guide adaptation for attachment to said object includes at least one resilient part that grips said object, said tapered tubular guide further comprising:
(f) a raised edge extending from said target end in a direction away from said open guide end whereby said raised edge contacts and exerts pressure on said target area of said object when said resilient parts grip said object.

9. The tubular guide of claim 8 wherein said tapered tubular guide is provided by a unitary piece of stainless steel and said stainless steel piece is fixedly attached to a holder that is adapted for attachment to said object so as to place said target end thereof aligned with and in registration with said relatively small target area of said object.

10. The tubular guide of claim 8 wherein said target area is part of the surface of a rubber diaphragm stopper.

11. The tubular guide of claim 10 wherein said diaphragm is a stopper of a vial containing liquid medication, and whereby the point of said syringe needle thrust into said guide is compelled to penetrate said target area of said rubber diaphragm stopper for access to said liquid medication.

* * * * *